US00PP31847P3

(12) United States Plant Patent
Kordes

(10) Patent No.: US PP31,847 P3
(45) Date of Patent: Jun. 9, 2020

(54) MINIATURE ROSE PLANT NAMED 'KORPOT088'

(50) Latin Name: *Rosa hybrida*
Varietal Denomination: KORpot080

(71) Applicant: W. KORDES' SÖHNE ROSENSCHULEN GMBH & CO. KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/501,728

(22) Filed: May 30, 2019

(65) Prior Publication Data

US 2019/0380241 P1 Dec. 12, 2019

(30) Foreign Application Priority Data

Jun. 6, 2018 (QZ) ..... 2018/1477

(51) Int. Cl.
*A01H 5/02* (2018.01)
*A01H 6/74* (2018.01)

(52) U.S. Cl.
USPC ..... Plt./123
CPC ..... *A01H 6/749* (2018.05)

(58) Field of Classification Search
USPC ..... Plt./123, 116, 118, 119, 125, 126
CPC ..... A01H 5/02
See application file for complete search history.

(56) References Cited

U.S. PATENT DOCUMENTS

PP23,845 P2 8/2013 Kordes
2019/0166740 P1 5/2019 Kordes

*Primary Examiner* — Kent L Bell
(74) *Attorney, Agent, or Firm* — Panitch Schwarze Belisario & Nadel LLP

(57) ABSTRACT

A new and distinct variety of Miniature Rose Plant, herein referred to by its cultivar name, 'KORpot088', is provided which forms attractive, orange-yellow-pink colored blossoms. The vegetation is vigorous and the growth habit is upright. Attractive ornamental foliage with good disease resistance is formed. The new variety is particularly well suited for providing distinctive ornamentation in the landscape.

1 Drawing Sheet

Botanical/commercial classification: Latin name—*Rosa hybrida. Common name—Miniature Rose Plant.*
Varietal denomination: 'KORpot088'.

CROSS-REFERENCE TO RELATED APPLICATIONS

This application claims priority to Plant Breeders' Right Application Number 2018/1477, which was filed at Community Plant Variety Office in the European Union on Jun. 6, 2018, the contents of which are hereby incorporated by reference for all purposes.

SUMMARY OF THE INVENTION

The new variety of *Rosa hybrida* Miniature Rose Plant of the present invention was discovered as a naturally occurring branch mutation of the variety, 'KORpot080' (U.S. Plant Pat. No. 30,845) during April, 2018 at Offenseth-Sparrieshoop, Germany It was found that the new Miniature Rose Plant of the present invention possesses the following combination of characteristics:

(a) forms attractive orange-yellow-pink colored blossoms,
(b) exhibits an upright growth habit,
(c) forms vigorous vegetation, and
(d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the parental variety, 'KORpot080', displays dark yellow color flowers, whereas the new variety displays orange-yellow-pink colored flowers. Moreover, the new variety can be readily distinguished from other similar non-parental varieties. For example, the 'KORbailand' variety (U.S. Plant Pat. No. 23,845) exhibits shorter flower duration and a lower petal count compared to the new variety and provides no noticeable fragrance, whereas the new variety exhibits some noticeable fragrance.

The new variety has been found to undergo asexual propagation in Klein Offenseth-Sparrieshoop, Germany by a number of routes such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot088'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a container.

FIG. 1—illustrates a specimen of the plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during March, while growing in a one-gallon container on its own roots in a greenhouse at Cochranville, Pa.

Class: Miniature Rose Plant.

Plant:

*Habit.*—Very upright.

*Height.*—Approximately 50.0 cm on average.

*Width.*—Approximately 30.0 cm on average.

Branches:

*Stem color.*—Commonly near Yellow-Green Group 144B.

*Main stem length.*—Approximately 50.0 cm on average.

*Secondary stem length.*—Approximately 22.0 cm on average.

*Surface texture.*—Glabrous.

*Thorns.*—Young thorns: moderate amount; length is approximately 6.0 mm on average, width is approximately 3.0 mm at point of attachment on average, and color is commonly near Red-Purple Group 58A. — old thorns: moderate amount; length is approximately 5.0 mm on average, width is approximately 1.0 mm at point of attachment on average, and color is commonly near Orange-Red Group 31C.

Foliage:

*Young foliage.*—Upper surface color: commonly near Greyed-Purple Group 187A with indistinguishable venation. — under surface color: commonly near Greyed-Purple Group 187B with indistinguishable venation.

*Old foliage.*—Upper surface color: commonly near Green Group 138A with Greyed-Purple Group 187A at margins, venation of near Greyed-Purple Group 187A. — under surface color: commonly near Green Group 138B with venation of near Greyed-Purple Group 186A for larger veins and near Green Group 138B for smaller veins.

*Petioles.*—Upper surface: texture is smooth, color is commonly near Yellow-Green Group 144A. — under surface: texture is mostly smooth with sparse prickles, color is commonly near Yellow-Green Group 146B.

*Rachis.*—Color: upper surface is commonly between near Yellow-Green Group 143C and 143A, under surface is commonly near Yellow-Green Group 143C.

*Stipules.*—Length: approximately 1.5 cm on average. — width: approximately 5.0 mm on average. — margin: entire to erose. — color: upper surface is commonly near Yellow-Green Group 144A; under surface is commonly near Yellow-Green Group 144B.

*Leaf margin.*—Serrate.

Leaflets:

*Number.*—3, 5, and 7.

*Arrangement.*—Odd pinnate.

*Shape.*—Ovate; apex is acute; and base is rounded.

*Venation.*—Pattern is reticulate.

*Texture.*—Upper surface is smooth; lower surface is smooth.

*Glossiness.*—Upper side of leaf is very-glossy.

*Size.*—Terminal leaflet: length is approximately 5.3 cm on average and width is approximately 3.3 cm on average. — lower leaflets: length is approximately 3.3 cm on average and width is approximately 2.2 cm on average. — 5-Leaflet leaf: length is approximately 12.5 cm on average and width is approximately 9.0 cm on average.

Inflorescence:

*Number of flowers.*—Approximately 10 blooms on average on a plant at once.

*Number of blooms per stem.*—Commonly 1 to 3 blooms per stem on average.

*Peduncle.*—Color: commonly Yellow-Green Group 144A. — diameter: approximately 7.0 mm on average. — length: approximately 3.5 cm on average. — surface texture: glabrous. — strength: strong.

*Sepals.*—Number: commonly 5. — upper surface color and texture: covered in short pubescence and color is commonly near Yellow-Green Group 144A. — under surface color and texture: puberulent and color is commonly near Yellow-Green Group 144A. — size: length is approximately 2.0 cm on average and width is approximately 7.0 mm on average. — shape: lanceolate; apex is acute to aristate; base is truncate or flat as it joins the receptacle. — margin: entire with occasional extensions on two or three sepals measuring approximately 7.0 mm in length and approximately 3.0 mm in width.

*Bud.*—Shape: globular. — size: length is approximately 1.5 cm on average; width is approximately 1.5 cm on average. — color when opening: commonly near Orange-Red Group 34B.

*Flower.*—Fragrance: light sweet fragrance. — form: double, cuplike. — profile: flat to slightly convex. — diameter: approximately 4.5 cm on average. — height: approximately 5.0 cm on average. — duration: commonly on the plant approximately 25 days on average. — petal color when first and fully open: upper surface is commonly near Yellow-Orange Group 21B with some blending of Orange-Red Group 32A on either side of the lower basal margin; under surface is commonly near Orange-Red Group 32A blending to near Orange Group 26A towards the apex and margins. — petal color when fading: upper surface is commonly near Yellow-Orange Group 21D with some blending of near Orange-Red Group 32C around the basal margins; and under surface is commonly near Yellow-Orange Group 23C with some blending of near Orange-Red Group 32C near the center and spreading through the basal margins.

*Petal.*—Number: approximately 42 on average. — drop: good. — length: inner petals are approximately 2.0 cm on average and outer petals are approximately 2.8 cm on average. — width: inner petals are approximately 1.8 cm on average and outer petals are approximately 3.5 cm on average. — shape: overall shape is broadly obovate; apex is round; and base is rounded to cuneate. — texture: upper and under surface is glabrous. — margin: entire.

*Petaloids.*—Number: approximately 2 per flower on average. — color: upper surface is commonly near Yellow-Orange Group 21B with some blending of near Orange-Red Group 32A near the margins; under surface is commonly a blend of near Yellow-Orange Group 21B and near Orange-Red Group 32A. — size: length is approximately 1.0 cm on average and width is approximately 1.0 cm on average. — texture: smooth. — margins: variable, entire to erose. — shape: rounded and mostly curving inward; apex is round, and base is rounded to cuneate.

*Stamen.*—Number: approximately 110 on average. — anthers: number is about 110; color is commonly near Yellow-Orange Group 17B; length is approximately 4.0 mm on average; and shape is oval. — filaments: length is approximately 5.0 mm on average and color is commonly near Yellow-Orange Group 17A.

*Pistils.*—Arrangement: separate and free. — number: approximately 90 on average. — style: color is mostly near Yellow Group 13D and exhibiting a small hint of near Orange-Red Group 34A at the base of the stigma; and length is approximately 3.0 mm on average. — stigma: color is commonly near Yellow-Orange Group 17C, diameter is typically less than 1.0 mm, and shape is fan shaped.

*Ovary.*—Length is approximately 2.0 mm, width is approximately 1.0 mm, and color is commonly near White Group 155D.

*Receptacle.*—Achenes stand on the bottom and wall; diameter is approximately 1.0 cm on average, shape is urn shaped, color is commonly near Yellow-Green Group 144A, and surface texture is smooth.

*Pollen.*—None observed.

*Hips/seed.*—None observed.

Development:

*Vegetation.*—Dark green, vigorous, and strong.

*Blooming.*—Abundant and continuous.

*Winter hardiness.*—Unknown.

*Resistance to disease.*—Good resistance to *Botrytis* (*Botrytis cinerea*) disease under normal greenhouse growing conditions in Cochranville, Pa.

Plants of the 'KORpot088' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive orange-yellow-pink colored blossoms, (b) exhibits an upright growth habit, (c) forms vigorous vegetation, and (d) forms attractive ornamental foliage with good disease resistance;

substantially as herein shown and described.

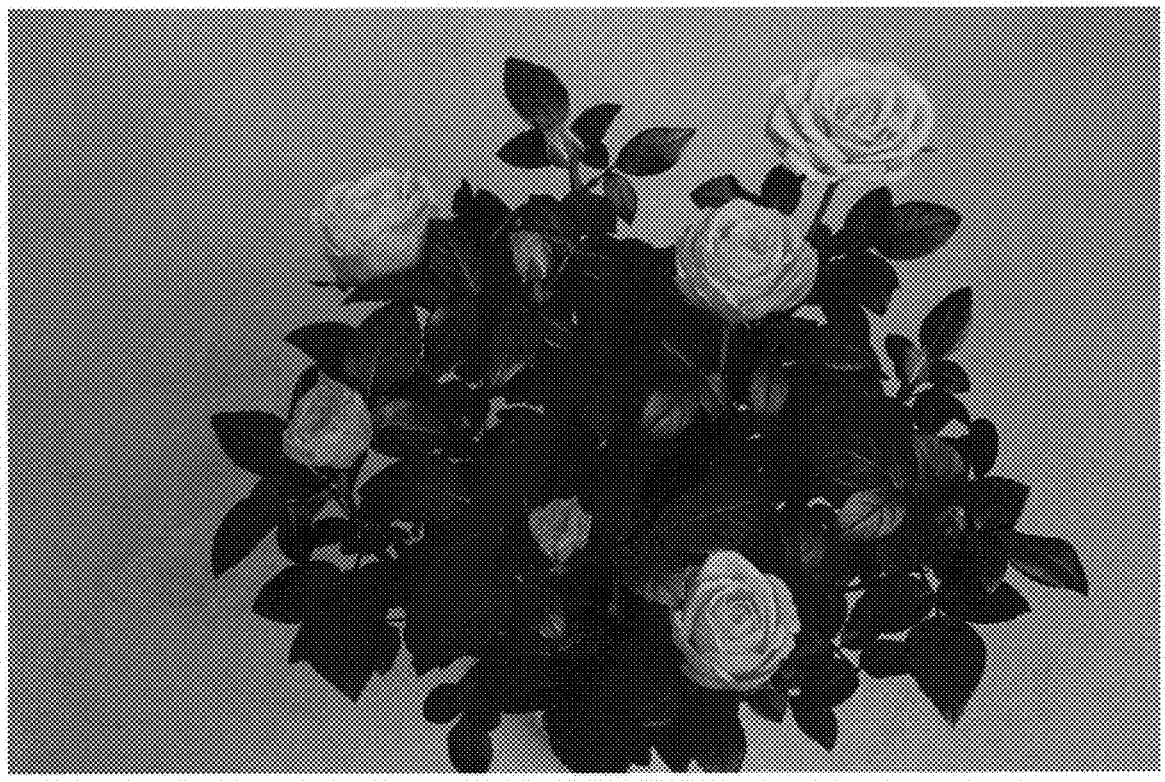

* * * * *